(12) United States Patent
Charoenvit et al.

(10) Patent No.: US 6,399,062 B1
(45) Date of Patent: Jun. 4, 2002

(54) MURINE MONOCLONAL ANTIBODY PROTECTIVE AGAINST *PLASMODIUM VIVAX* MALARIA

(75) Inventors: Yupin Charoenvit, Silver Spring; Stephen L. Hoffman, Gaithersburg; Richard L. Beaudoin, deceased, late of Rockville, all of MD (US), by Barbara A. Beaudoin, administrator

(73) Assignee: The United States of America as represented by the Secretary of the Navy, Washington, DC (US)

(*) Notice: Subject to any disclaimer, the term of this patent is extended or adjusted under 35 U.S.C. 154(b) by 0 days.

(21) Appl. No.: 08/176,024

(22) Filed: Dec. 28, 1993

Related U.S. Application Data

(63) Continuation-in-part of application No. 07/609,549, filed on Nov. 6, 1990, now abandoned.

(51) Int. Cl.$^7$ ............................................. A61K 39/395
(52) U.S. Cl. ................. 424/134.1; 424/139.1; 424/141.1; 424/151.1; 530/387.3; 530/388.6
(58) Field of Search .......................... 530/387.3, 388.6; 424/134.1, 139.1, 141.1, 151.1

(56) References Cited

U.S. PATENT DOCUMENTS

| 4,693,994 A | * | 9/1987 | McCutchan | .................. | 514/15 |
| 5,095,093 A | * | 3/1992 | Hoffman et al. | ............. | 530/330 |

FOREIGN PATENT DOCUMENTS

| WO | 8601533 | * | 3/1986 |
| WO | 9109967 | * | 7/1991 |

OTHER PUBLICATIONS

Barr et al. J Exp Med 16S:1160–1171, 1987.*
Hollingdale et al. J Immunol. 132:909–913, 1984.*
Naradin et al. J. Exp. Med 156:20–30, 1982.*
Co et al. Nature 351:501–2, 1991.*
Harris et al. Tibtech 11:42–44, 1993.*
Queen et al. PNAS USA 86:10029–33, 1989.*
Morrison et al. PNAS USA 81:6851–6855 1984.*
Mitchell, Parasitology vol 98 supplement 529–547, 1989.*
Cunningham et al. Tibtech 10, 1992.*
Harris et al. Tibtech 11:42–43, 1993.*
Gibbs, Scientific American Jul. 1993 101–103.*
Charoenvit et al. Science 251:668–671, 1991.*
Lerner, Nature 299:592–596, 1982.*
Harlow et al. "Antibodies A Laboratory Manual" Cold Spring Harbor Laboratory, 1988, p. 287.*
McCutchan et al. Science 230:1381–1383, 1985.*
Egan et al. Science 236:453–456, 1987.*
Charoenvit et al. Infect. & Immunity 55:604–608, 1987.*
Potocnjak et al. J. Exp. Med. 151:1504–1513, 1980.*
Morrison, Science 229:1202–1207, 1985.*
Waldmann, Science 252:1657–1662, 1991.*

* cited by examiner

*Primary Examiner*—Sheela Huff
(74) *Attorney, Agent, or Firm*—A. David Spevack; Charles H. Harris

(57) ABSTRACT

The invention relates to a passive protective agent against *P. vivax*. The passive protective agent is an antibody that, when a concentration of the antibody is injected intravenously, protects a subject to the limits of that concentration of antibody from developing malaria when the subject is subsequently challenged with live, infectious *P. vivax* sporozoites. The invention includes methods of treatment and pharmaceutical formulations of the agent.

9 Claims, 3 Drawing Sheets

MURINE MONOCLONAL ANTIBODY PROTECTIVE AGAINST *PLASMODIUM VIVAX* MALARIA

This is a continuation-in-part of application Ser. No. 07/609,549 filed Nov. 6, 1990, now abandoned.

SPECIFICATION

DEPOSIT INFORMATION

The Hybridoma, NVS3 (Navy Vivax Sporozite 3) is deposited in the American Type Culture Collection (ATCC), 10801 University Blvd., Manassas, Va. 20110-2209, USA, by a deposit received Nov. 30, 1990, under the terms and conditions of the Budapest treaty for a period of thirty (30) years. The ATCC designation number is HB 10615, Under the terms of the deposit access to the culture will be available during pendency of the patent application to one determined by the Commissioner of Patents and Trademarks to those found to be entitled thereto under 37 CFR 1.14 and 35 U.S.C. 122, and all restrictions on the availability to the public of the culture will be irrevocably removed upon grant of the Patent.

BACKGROUND OF THE INVENTION

1. Field of the Invention

This invention relates to a passive protective agent against *P. vivax*. More particularly this invention relates to an antibody that, when a concentration of the antibody is injected intravenously, protects a subject to the limits of that concentration of antibody from developing malaria when the subject is subsequently challenged with live, infectious *P. vivax* sporozoites.

2. Description of the Prior Art

There have been major efforts toward development of malaria vaccines undertaken during the past 20 years. Although a commercially viable vaccine has not been achieved to the time this application is filed, there have been successes in providing vaccine protection. The continued vast investment in vaccine research by both governments world wide and industry shows an expectation of achieving a commercially viable vaccine. A commercially viable vaccine is one that provides protection with minimum side effects, is capable of being produced in quantity, and is stable in storage for a reasonable time under reasonable conditions. These conditions and requirements are well known in the medical and pharmaceutical arts. Even the near misses of total successes (e.g. successes with only a small population) are useful in understanding the mechanisms of malaria and further defining the parameters that will lead to a commercially successful vaccine or treatment. The current status of malaria vaccine development has been summarized in a recent Institution of Medicine Report[1]. The introduction to the section on vaccines is included verbatim to provide part of the background for this application.

WHERE WE ARE TODAY

Prospects for a Vaccine

Vaccination is an exceptionally attractive strategy for preventing and controlling malaria. Clinical and experimental data support the feasibility of developing effective malaria vaccines. For example, experimental vaccination with irradiated sporozoites can protect humans against malaria, suggesting that immunization with appropriate sporozoite and liver-stage antigens can prevent infection in individuals bitten by malaria-infected mosquitoes. In addition, repeated natural infections with the malaria parasite induce immune responses that can prevent disease and death in infected individuals, and the administration of serum antibodies obtained from repeatedly infected adults can control malaria infections in children who have not yet acquired protective immunity. These data suggest that immunization with appropriate blood-stage antigens can drastically reduce the consequences of malaria infection. Finally, experimental evidence shows that immunization with sexual-stage antigens can generate an immune response that prevents parasite development in the vector or, offering a strategy for interrupting malaria transmission.

Prospects for the development of malaria vaccines are enhanced by the availability of suitable methods for evaluating candidate antigens. These include protocols that allow humans volunteers to be safely infected with malaria, and the identification of many areas in the world where more than 75 percent of individuals can be expected to become infected with malaria during a three-month period. In contrast to vaccine for disease of low incidence, for which tens of thousands of immunized and non-immunized controls must be studied over several years, malaria vaccines could be evaluated in selected areas in fewer than 200 volunteers in less than a year.

Developments in molecular and cellular biology, peptide chemistry, and immunology provide the technological base for engineering subunit vaccines composed of different parts of the malaria parasite, an approach that was not possible 10 years ago. During the past 5 years, more than 15 experimental malaria vaccines have undergone preliminary testing in human volunteers. Although none of these vaccines has proven suitable for clinical implementation, progress has been made in defining the parameters of a successful vaccine and the stage has been set for further advancement.

Despite the inherent attractiveness and promise of this approach, there remain a number of obstacles to vaccine development. With the exception of the erthrocytic (blood) stages of *P. falciparum*, human malaria parasites cannot be readily cultured in vitro, limiting the ability of researchers to study other stages of this parasite and all stages of the other three human malaria parasite species.

In vitro assays, potentially useful for screening candidate vaccines for effectiveness, do not consistently predict the level of protective immunity seen in vivo. The only laboratory animals that can be infected with human malaria parasites are certain species of nonhuman primates, which are not naturally susceptible to these organisms. This makes it difficult to compare the results of many studies done in animals with what happens in human malaria infection.

The promises of modern vaccinology, while potentially revolutionary, have so far proved elusive. Few commercially available vaccines have been produced by this technology, for both scientific and economics reasons. Scientists have not yet been able to assemble defined synthetic peptides and recombinant proteins and combine them with new adjuvants and delivery systems into a practical human malaria vaccine. However, as discussed above and in the remainder of this chapter, there are good reasons to believe that this approach will ultimately succeed.

Approaches to Vaccine Development

The complex life cycle of the malaria parasite provides a number of potential targets for vaccination. Under investigation are vaccines that would be effective against the extracellular sporozoite, during the short period it spends in the bloodstream; the exoerythrocytic (or liver-stage) parasite, during the roughly seven days it develops within liver cells; the extracellular merozoite, released from liver cells or infected erthrocytes and free in the circulation prior to invading other erthrocytes; the asexual parasite that develops within red blood cells; exogenous parasite material released from infected erthrocytes; and the sexual-stage parasite, which occurs both inside erythrocytes and in mosquitoes. The optimal vaccine would include antigens from the sporozoite, asexual, and sexual stages of the parasite, thus providing multiple levels of control, but vaccines effective against individual stages could also prove highly useful. In addition, a vaccine against the Anopheles mosquito itself, which reduced the insect's life span and prevented complete development of the parasite, could be valuable.

Regardless of the stage of parasite targeted for vaccine development, a similar strategy is envisioned. Based on knowledge of the mechanisms of protected immunity, specific parasite antigens (immunogens) are identified that induce a protective immune response, and synthetic or recombinant vaccines that accurately mimic the structure of that antigen are prepared.

In the subunit approach to vaccine development, this is done by combining the immunogen with carrier proteins, adjuvants, and live vectors or other delivery systems. This approach is being pursued throughout the world in laboratories studying infectious diseases. Clinical utility has yet to be demonstrated for the majority of these efforts, and barriers to obtaining satisfactory immunization by the subunit approach remain. Nevertheless, research on malaria subunit vaccines will continue to be at the cutting edge of this innovative and important approach to vaccine development.

It is clear from this description that major advances have been made, and many parasite proteins that could be targets of vaccine development have been identified. What has been lacking is an effective, economically feasible method for inducing protective immune responses against these already identified proteins. Perhaps the most striking example has been in the field of pre-erythrocytic stage malaria vaccine development in which there is already an effective vaccine for humans, the irradiated sporozoite vaccine, but the vaccine is totally impractical for widespread human use because of production and administration problems.

The Irradiated Sporozoite Model

In the 1940s, Mulligen and colleagues[2] demonstrated that immunization of chickens with radiation attenuated *Plasmodium gallinaceum* sporozoite induced protective immunity. In the late 1960s, Nussenzweig and collegues[3] demonstrated that immunization of A/J mice with radiation attenuated *P. berghei* sporozoite protected mice against challenge with infected erythrocytes were not protected. In the early 1970s Clyde and colleagues[4-6] and Rieckmann and colleagues[7,8] demonstrated that immunization of humans by the bite of irradiated Anopheles species mosquitoes carrying *P. falciparum* and in one case *P. vivax* sporozoites in their salivary glands protected these volunteers against challenge with live sporozoites. Like the immunity in mice, this immunity was stage specific, and it was also species specific; immunization with *P. falciparum* did not protect against *P. vivax* . However, it was not strain specific; immunization with *P. falciparum* sporozoites from Burma protected against challenge with sporozoites from Malaya, Panama and the Philippines[4], and immunization with sporozoites from Ethiopia protected against challenge with a strain from Vietnam[8]. These human studies have been repeated recently[9,10] reconfirming that there already is an effective malaria vaccine, and demonstrating this protective immunity lasts for at least 9 months[11]. Unfortunately, sporozoites have to be delivered alive, and since mature, infective sporozoites-infected mosquitoes, the targets and mechanisms of this protective immune response had to be identified so as to construct a synthetic or recombinant vaccine.

Of the four human malarias, *P. vivax* and *P. falciparum* are the most common and cause the majority of the malaria-induced disease seen worldwide. Prevention of infection by these human parasites would alleviate a major health problem in the tropical and subtropical areas of the world. The most promising method for the control of malaria appears to be the development and use of vaccines. One approach to malaria vaccine development involves the use of the circumsporozoite (CS) protein as a vaccine antigen. This protein covers the surface of the sporozoite. The sporozoite is the life stage of the parasite which is transmitted to humans by feeding female Anopheline mosquitoes. Evidence from both mouse and human malarias indicates that antibodies to the CS protein can provide protection in vivo against infection by sporozoites (Charoenvit et al., Infect. Immunity 55:604, 1987; Charoenvit et al., *J. Immunol.,* 146, pp. 1020–1025, (1991). Khusmith et al., *Science,* 252, pp. 715–718, (1991).

In 1985, McCutchan and colleagues sequenced the gene for the CS protein in *P. vivax* and determined the amino acid sequence derived from that gene, (McCutchan et al., Science 230:1381, 1985). The monoclonal antibody originally used by McCutchan and colleagues (McCutchan et al., Science 230:1381, 1985) to identify the protein and isolate the nucleotide sequence which later became the subject of the McCutchan/Wistar U.S. Pat. No. 4,693,994 was originally developed by Charoenvit and Beaudoin of the Infectious Diseases Department, Naval Medical Research Institute (NMRI). This monoclonal antibody is the monoclonal antibody of this invention. It has been named or designated MAB Navy Vivax Sporozoite 3 (NVS3). In 1987, McCutchan and Wistar, in U.S. Pat. No. 4,693,994, described a repeated nine amino acid sequence within the CS protein as an immunodominant synthetic peptide. The repeated sequence is Gly-Asp-Arg-Ala-Asp-Gly-Gln-Pro-Ala.

In the '994 patent and in other publications, McCutchan/Wistar maintain that the nine amino acid sequence is capable of inducing antibodies protective against *P. vivax* malaria. Experimental evidence indicates that while the McCutchan/Wistar sequence stimulates the development of anti-CS antibody in humans, it has not been shown to induce protective antibodies. In an article published in Am. J. Trop. Med. Hyg. 40(5), p455–464 (1989), Collins et al. describes tests in which Saimiri monkeys (*Saimiri sciureus boliviensis*), which are susceptible to human vivax malaria, were immunized with two different preparations (VIVAX-1 and $NS1_{81}V20$). Both preparations contain the McCutchan/Wistar peptide (Gly-Asp-Arg-Ala-Asp-Gly-Gln-Pro-Ala). When these monkeys were challenged with $10^4$ *P. vivax* sporozoites, there was no significant protection.

Nussenzweig et al., in U.S. Pat. No. 4,826,957, describes an immunogenic recombinant yeast expression product which contains a long sequence incorporating a portion of the *P. vivax* circumsporozite. The Nussenzweig et al. sequence contains multiple repeats of the sequence Gly-Asp-Arg-Ala-Asp-Gly-Gln-Pro-Ala as part of a complex polypeptide. When used as a vaccine, this polypeptide causes the formation of antibodies, the antibodies are directed at Gly-Asp-Arg-Ala-Asp-Gly-Gln-Pro-Ala and did not provide significant protection against challenge with sporozoites.

In U.S. Pat. No. 4,957,869, Arnot et al. describes an immunogenic peptide corresponding to *P. vivax* CS protein consisting of at least two repeats of the amino acid sequence Asp-Arg-Ala-X-Gly-Gln-Pro-Ala-Gly. X is defined as selected from the group consisting of Asp and Ala. The prior art approachs the problem from the premise that a vaccine is needed to provide protection against malaria. There is also a need for a simple material to protect against P. vivax.

SUMMARY OF THE INVENTION

Accordingly, an object of this invention is a monoclonal antibody which provides passive protection against P. vivax.

Another object of the invention is a pharmaceutical preparation which provides passive protection against P. vivax.

An additional object of this invention is a means of providing temporary or limited protection against P. vivax by binding a particular site on the CS protein of P. vivax and thereby preventing infection by sporozoites of that parasite.

A further object of this invention is an agent to produce and isolate a human protective antibody against P. vivax.

Yet an additional object of this invention is a method of using the unique binding and protective nature of the mouse monclonal antibody as a special reagent for conversion into a human monoclonal antibody which retains the same binding specificity and can therefore be used in humans to induce temporary antibody-mediated passive immunity.

Other objects and advantages of this invention will become clear as the detailed description of the present invention is presented. These and additional objects of the invention are accomplished by a murine, IgG3 monoclonal antibody designated NVS3 produced by immunizing mice with irradiated P. vivax sporozoites and pharmaceutical preparations of NVS3 which neutralize infectious sporozoites of P. vivax.

BRIEF DESCRIPTION OF THE DRAWINGS

A more complete appreciation of the invention will be readily obtained by reference to the following Description of the Preferred Embodiments and the accompaning drawings in which like numerals in different figures represent the same structures or elements. The representations in each of the figures is diagrammatic and no attempt is made to indicate actual scales or precise ratios. Proportional relationships are shown as approximations.

DESCRIPTION OF THE PREFERRED EMBODIMENTS

Figure 1:
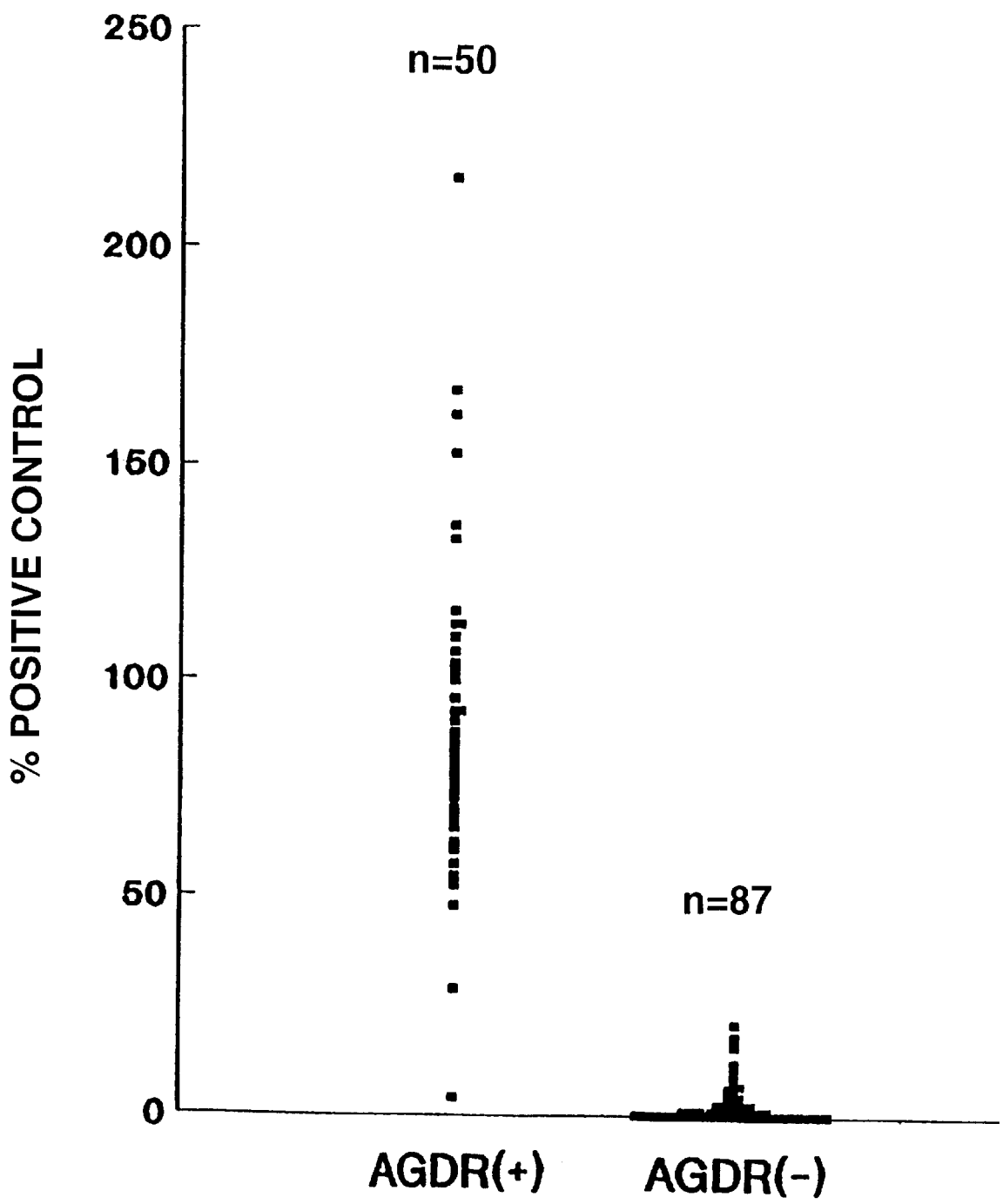
FIG. 1 is a graph plotting antibody-octapeptide reactivity of peptides containing the entire AGDR sequence (AGDR+) and those with part or none (AGDR−) against percent of the optical density of the positive control.

The present invention rests on the development of a monoclonal, antibody designated NVS3 which binds to a particular epitope on the CS protein of the sporozoite of the human malaria parasite P. vivax. NVS3 (Navy vivax sporozoite 3) is an IgG3 isotype antibody. It is species and stage specific; it reacts only with sporozoites of P. vivax, and does not react with sporozoites of P. falciparum, P. berghei, P. yoelii, or P. gallinaceum. It is also nonreactive with blood stages of P. vivax, P. falciparum, P. berghei, P. yoelii and P. gallinaceum when tested in an immunofluorescent antibody technique (IFAT). NVS3 is not strain specific. It reacts with sporozoites from other strains of P. vivax (i.e. North Korean, Sal 1, Colombian, and Thai strains). Western blot analysis of a P. vivax sporozoite extract showed that NVS3 reacted with four antigen bands with relative molecular weights of 46, 49, 50 and 57 kda. The monoclonal antibody-producing cell, Hybridoma, NVS3 (Navy Vivax Sporozoite 3), was submitted for deposit Nov. 30, 1990, under the provisions of the Budapest Treaty, with the American type Culture Collection (ATCC), 10801 University Blvd., Manassas, Va. 20110-2209, USA. Its deposit number is HB10615. The MAB is available from the ATCC when this application issues as a patent or upon request to the Navel Medical Research Institute, Bethesda Md. 20889-5055. NVS3 is produced through known techniques by immunization with irradiated, but otherwise intact sporozoite, and not by a recombinant protein.

The unique specificity of this antibody permits pharmaceutical formulations of the antibody to be administered to a host subject where the antibody binds to P. vivax sporozoites in the circulation of the host and renders the sporozoites noninfectious thereby preventing malaria disease. The adjuvants and diluents are the pharmaceutical materials usually used for this type of protein material. The dosage will vary with the subject receiving it.

The unique aspect of this NVS3 antibody lies in the conformation of the antigen binding site (complementarity determining regions or hypervariable regions) of the heavy and light chains of the IgG molecule. Current technology permits the conversion of this mouse IgG molecule into a human IgG molecule which still retains the same antigen binding specificity. Conversion allows the use of the NVS3 antibody as a passive immunization agent similar to the hyperimmune gamma-globulin used to passively immunize against hepatitis A.

The production of a mouse-human "chimeric" or a "humanized" mouse Mab requires as a starting point a biologically active (in this case "protective") variable or hypervariable region of a mouse Mab. It should be noted that in the case of Mabs against circumsporoziote proteins, it is only this region that is required since Fab fragments provide protection in passive transfer. There are a number of published strategies that are employed to accomplish this humanization. The work is routine but tedious. Using NVS3 cell line one would extract RNA and use known primers to produce heavy and light chain variable region cDNAs. These would be sequenced using standard methods or machines. The heavy and light chain CDR sequences are predicted using established methods and alignment with other known heavy and light chain CDR sequences. Having established the sequence of the framework region of the variable region, one scans databases to identify sequences of human IgG with homology to the variable framework region of NVS3 . One would then synthesize heavy and light chains that include the NVS3 CDR sequences and the homologous human IgG framework.

Epitope mapping studies demonstrated that NVS3 recognizes only four (Ala-Gly-Asp-Arg (AGDR)) of the nine amino acids (DRA A/D GQPAG) within the repeat region of the P. vivax circumsporozoite protein. Sera from monkeys immunized with a recombinant protein did not produce antibodies to this protective epitope. They did, however, produce high levels of antibodies to other epitopes in the repeat region. The data clearly demonstrate that circulating antibodies to a defined epitope on the *P. vivax* CS protein can protect against malaria in vivo, and indicate that determination of the fine specificity of protective antibodies and the construction of subunit vaccines to exclude irrelevant amino acid residues may be critical to the induction of antibodies having the appropriate specificity for mediating protective immunity. The invention pertaining to the AGDR sequence is the subject of a concurrently filed application number 609,551 filed in the names of Hoffman, Charoenvit, and Jones and titled PROTECTIVE FOUR AMINO ACID EPITOPE AGAINST PLASMODIUM VIVAX MALARIA now U.S. Pat. No. 5,095,093, issued Mar. 10, 1992.

It is noted that those technical terms or phrases used here which have not been specifically defined have the same meaning as generally understood by one of ordinary skill in the art to which this invention belongs.

Having described the invention, the following examples are given to illustrate specific applications of the invention including the best mode now known to perform the invention. These specific examples are not intended to limit the scope of the invention described in this application.

EXAMPLE 1

Materials and Methods

Animals

Female, 6–8 week old, BALB/c Byj mice (Jackson Laboratories, Bar Harbor, Me.) were used in the production of monoclonal antibodies. *Saimiri sciureus boliviensis* monkeys were used in the passive transfer study to evaluate the protective efficacy of a selected monoclonal antibody. The monkeys were of Bolivian origin. All animals were quarantined for a one-month conditioning period, weighed, tested for tuberculosis and examined for concurrent intestinal and blood stage infections.

Sporozoites

*P. vivax* sporozoites of the Vietnam strain (ONG/CDC), North Korean (NK) and Colombian strains were used for production and characterization of the monoclonal antibodies. Sporozoites were separated from infected *Anopheles stephensi* mosquitoes by a discontinuous gradient technique described by Pacheco, N. D., C. P. A. Strome, F. Mitchell, M. P. Bawden and R. L. Beaudoin; Rapid, large-scale isolation of *Plasmodium berghei* sporozoites from infected mosquitoes; *J. Parasitol*; 65:414–417; 1979. Sporozoites of the Salvador I strain were reared in *A. stephensi* mosquitoes by membrane feeding the mosquitoes on blood from a gametocytemic chimpanzee as described by Collins, W. E., H. M. McClure, R. B. Swenson, P. C. Mehaffey and J. C. Skinner; Infection of mosquitoes with *Plasmodium vivax* from chimpanzees using membrane feeding. *Am. J Trop. Med. Hyg.*; 35:56–60; 1986. Sixteen days post-feeding, the sporozoites were dissected from the salivary glands of the infected mosquitoes for use in the challenge studies.

EXAMPLE 2

Production and Characterization of Monoclonal Antibodies

Mice were immunized intravenously at weekly intervals with $3-5 \times 10^4$, radiation attenuated ($10^4$ rads) sporozoites. Three days after the third immunization, spleen cells were isolated and fused with X63.Ag8.653, non-immunoglobulin secretor mouse myeloma cells using the well known method described by Kohler and Milstein (75) with a slight modification. Briefly, spleen cells isolated from immunized mice were fused with myeloma cells using 30% polyethylene glycol (approximate mol. wt. 1000) as a fusing agent. The cells were washed, resuspended in HAT selective medium and plated into 96-well tissue culture plates and allowed to grow at 37° C. in 5% $CO_2$ in air. Three weeks later the supernatants from the growth wells were screened for antibodies to *P. vivax* sporozoites using an immunofluorescent antibody technique (IFAT) as described by Charoenvit, Y., M. F. Leef, L. F. Yuan, M. Sedegah and R. L. Beaudoin; Characterization of *Plasmodium yoelii* monoclonal antibodies directed against stage-specific sporozoite antigens; *Infect. Immunol.*; 55:604–608; 1987. The positive hybrids were cloned by limiting dilution, and the supernatants from the wells containing hybridoma clones were retested. IFAT positive clones were expanded for the production of ascitic fluid; monoclonal antibodies of interest were purified from ascitic fluid. Double immunodiffusion against goat anti-mouse immunoglobulins was used to determine isotype. Species and stage specificities were determined in an immunofluorescent antibody technique against sporozoites and blood stage parasites from *P. vivax, P. falciparum, P. berghei, P. yoelii* and *P. gallinaceum*. Reactivity to different strains of *P. vivax* (North Korean, Salvador 1, Colombian and Thai) was also measured. Western blot analysis was used to determine the number of proteins in the sporozoite to which the monoclonal antibody selected for passive transfer binds. The selected antibody was designated NVS3 (Navy Vivax Sporozoite 3). It was purified by staphylococcal protein A column as described by Hjelm, H. and J. Sjoquist; The use of matrix-bound protein A from *Staphylococcus aureus* for the isloation and determination of immunoglobulins; In: Immunoadsorbents in Protein Purification; E. Ruoslahti, editor. University Park Press, Inc. Baltimore; pp.51–57; 1976. The cell line producing the NVS3 is deposited with the American Type Culture Collection. The accession number is HB10615.

EXAMPLE 3

Sporozoite Challenge Study

An initial set of experiments was performed to determine the amount of intravenously injected NVS3 required to achieve antibody levels which gave responses in an enzyme-linked immunosorbant assay (ELISA) similar to sera from monkeys immunized with $NS1_{81}V20$ reported by Collins, W. E., R. S. Nussenzweig, W. R. Ballou, T. K. Ruebush II, E. H. Nardin, J. D. Chulay, W. R. Majarian, J. F. Young, G. F. Wasserman, I. Bathurst, H. L. Gibson, P. J. Barr, S. L. Hoffman, S. S. Wasserman, J. R. Broderson, J. C. Skinner, P. M. Procell, V. K. Filipski and C. L. Wilson; Immunization of *Saimiri sciureus boliviensis* with recombinant vaccines based on the circumsporozoite protein of *Plasmodium vivax*; *Am. J Trop. Med. Hyg.*; 40:455–464; 1989. Based on these experiments, 2 mg of NVS3 per monkey was selected for injection intravenously into six Saimiri monkeys. Of course the dosage can vary from 2 to 30 mg dependant on weight and metabolism of the subject.

An IgG3 monoclonal antibody directed against *Trypanosoma brucei rhodesiense* in accordance with the method described by Hall, T. and K. Esser; Topologic mapping of protective and nonprotective epitopes on the variant surface glycoprotein of the WRATat 1 clone of *Trypanosoma brucei rhodesiense*; *J. Immunol.*; 132:2059–2063; 1984 was inoculated into another six monkeys to serve as an unrelated antibody control group. Nine other monkeys served as uninjected controls. One hour after antibody transfer, $10^4$ *P. vivax* sporozoites diluted in normal saline containing 10% normal Saimiri monkey serum were injected into all monkeys. Serum samples were collected prior to antibody inoculation and one hour later (immediately before sporozoite challenge). All animals were splenectomized 6 to 7 days after sporozoite inoculation. Beginning 14 days after sporozoite inoculation and continuing through day 56, giemsa-stained thick and thin blood films were prepared daily. Parasitemias were quantified and recorded per $mm^3$ of blood.

Four of the six monkeys inoculated with NVS3 were fully protected against blood stage disease. The remaining two developed patent parasitemias after 31 and 40 days (Table 1). Five of six monkeys inoculated with the unrelated monoclonal antibody (anti-trypanosoma) developed detectable parasitemias within IS to 24 days (mean=20.6 days) while the nine control monkeys all developed detectable parasitemias in 17 to 30 days (mean=20.1 days). The two unprotected monkeys that received NVS3 had longer pre-patent periods than the control monkeys which received the anti-trypanosoma antibody ($p<0.01$) and longer than the uninjected controls ($p<0.005$). At splenectomy, the spleens were observed to be enlarged in animals of both groups that received the monoclonal antibodies. None of the nine untreated control animals had an enlarged spleen.

EXAMPLE 4

Epitope scanning

A hypothetical peptide containing the repeat regions of the CS proteins of 4 strains of P. vivax was designed. The four strains were Belem (Arnot, D. E., J. W. Barnwell, J. P. Tam, V. Nussenzweig, R. S. Nussenzweig and V. Enea; Circumsporozoite protein of Plasmodium vivax gene cloning and characterization of the immunodominant epitope; Science; 230:815–818; 1985), Sal 1 (McCutchan, T. F., A. A. Lal, V. F. de la Cruz, L. H. Miller, W. L. Maloy, Y. Charoenvit, R. L. Beaudoin, P. Guerry, R. Wistar, Jr., S. L. Hoffman, W. T. Hockmeyer, W. E. Collins and D. Wirth; Sequence of the immunodominant epitope for the surface protein on sporozoites of Plasmodium vivax; Science; 230:1381–1383; 1985), North Korean (Arnot, D. E., J. W. Barnwell and M. J. Stewart; Does biased gene conversion influence polymorphism in the circumsporozoite protein-encoding gene of Plasmodium vivax; Proc. Natl. Acad. Sci. USA; 85:8102–8106; 1988) and VS 210 (Rosenberg, R., R. A. Wirtz, D. E. Lanar, J. Sattabongkot, Ti Hall, A. P. Waters and C. Prasittisuk; Circumsporozoite protein heterogeneity in the human malaria parasite Plasmodium vivax; Science; 245:973–976; 1989). The sequence of the peptide is as follows: GDRADGQPAGDRADGQPAGD RADGQAAG-NGAGGQPAGDRAAGQPAGD-GAAGQPAGDRADGQPAGDRAAGQP AGDRADGQPAGDRADGQAAGNGAG-GQAAGNGAGGQPAGDRAAGQPAGD RAAGQPAGDRAAGQAAGNGAGGQAA. The methods of Geysen and colleagues described in Use of peptide synthesis to probe viral antigens for epitopes to a resolution of a single amino acid; Proc. Natl. Acad. Sci. USA; 81:3998–4002; 1984; Small peptides induce antibodies with a sequence and structural requirement for binding antigen comparable to antibodies raised against the native protein; Immunol; 82:178–182; 1985; A priori delineation of a peptide which mimics a discontinuous antigenic determinant; Molec. Immunol; 23:709–715; 1986; Strategies for epitope analysis using peptide synthesis; J. Immunol. Methods; 102:259–274; 1987 were employed to synthesize 137 sequential octapeptide subsets of this 144 amino acid peptide. The octapeptides were synthesized on the tips of polypropylene pins set in 96 pin blocks (Cambridge Research Biochemicals, Valley Stream, N.Y.). Octapeptide n=amino acid n through amino acid n+7. The syntheses were carried out in the wells of 96 well plates thereby allowing each pin to hold a different amino acid sequence. Conventional Fmoc solid phase methods were used to complete the syntheses. The tetrapeptides PLAQ (and monoclonal antibody to it) and GLAQ were used as positive and negative controls in each set of 96 pins. The ability of the monoclonal antibody NVS3 to bind to the peptides was tested in an ELISA. Each pin was incubated overnight at 4° C. in NVS3 at 2 μg antibody/ml. After washing, the pins were incubated for one hour at 37° C. in goat anti-mouse IgG (Kirkegaard and Perry, Gaithersburg, Md.) at a dilution of 1:2000. Optical densities were measured after the pins were incubated in substrate (ATBS, 2,2'-azino-di-[3-ethyl-benzthiazoline sulfonate] and hydrogen peroxide) for 30 minutes.

Analysis of the ELISA results revealed a correlation between NVS3-octapeptide binding and the presence of the tetrapeptide AGDR (alanine-glycine-aspartic acid-arginine) (FIG. 1 in which antibody-octapeptide reactivity of peptides containing the entire. AGDR sequence (AGDR+) and those with part or none (AGDR–) is plotted against percent of the optical density of the positive control. The n values are the total number of octapeptides containing AGDR (50) and not containing AGDR (87). The positive control optical density was obtained with an anti-PLAQ monoclonal antibody.).

Figure 2:
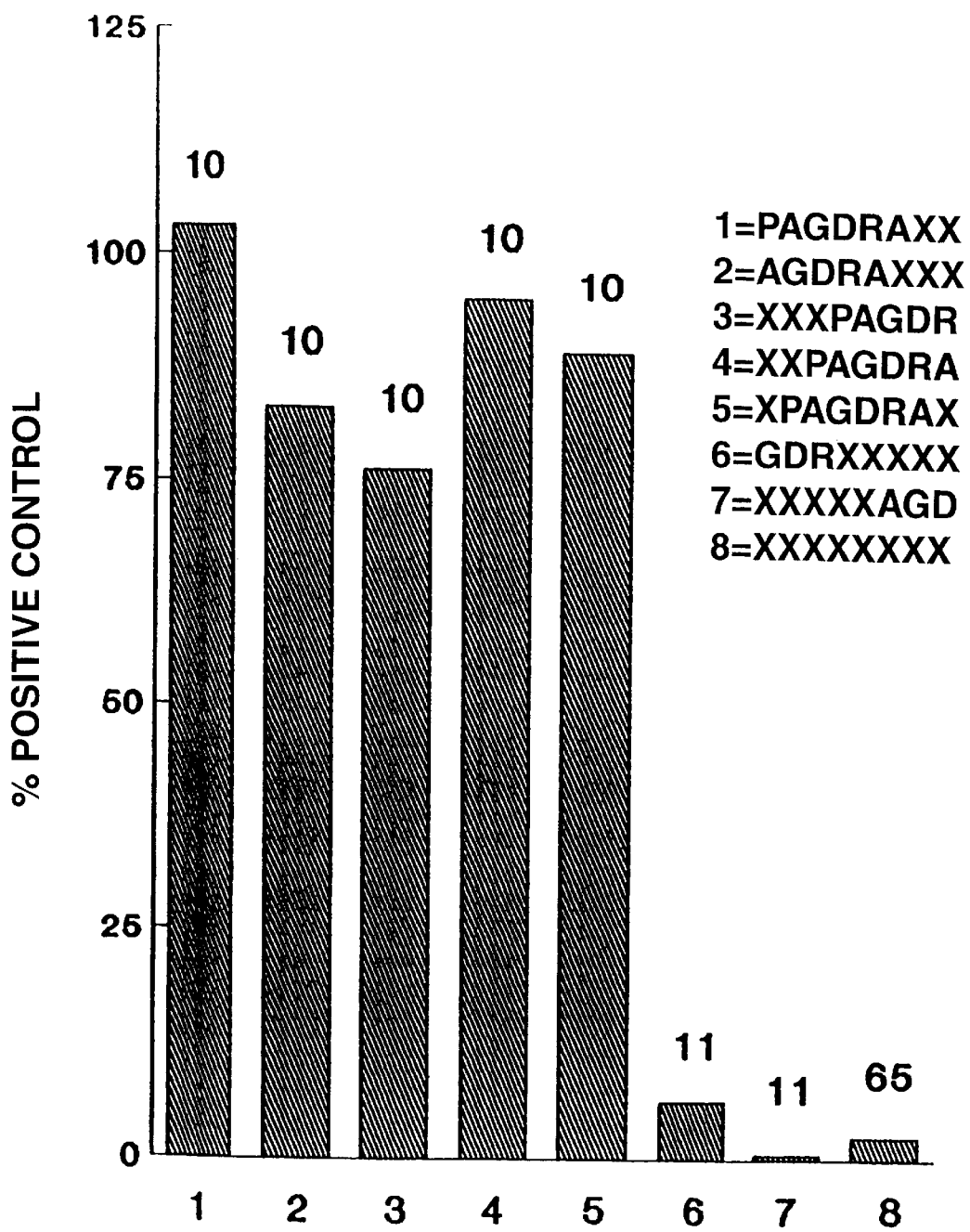
FIG. 2 is a bar chart in which antibody-peptide binding is expressed as the percent of the positive control optical density (OD of anti-PLAQ monoclonal antibody with PLAQ).

Octapeptides not containing the sequence AGDR were not bound by NVS3. Octapeptides containing subsets of AGDR (e.g. AGD and GDR) were also not reactive. No correlation between reactivity and the location of tetrapeptide within the octapeptide was noted (FIG. 2 in which antibody-peptide binding is expressed as the percent of the positive control optical density (OD of anti-PLAQ monoclonal antibody with PLAQ). Bars one through eight represent the mean binding of peptides having the sequences shown in the inset. The number above each bar is the n of that group.).

EXAMPLE 5

The following materials are needed for tests.

Peptide Synthesis

The 8-residue peptide $(AGDR)_2$ was synthesized by the stepwise solid-phase method of Merrifield, R. B; Solid phase peptide synthesis. I. The synthesis of a tetrapeptide; *J. Am. Chem. Soc.;* 85:2149–2154; 1963. Pam-t-Boc-L-arginine (Tos) resin (0.5 used as the starting point of the synthesis. The protected peptide resin was deprotected by hydrogen fluoride/p-cresol (9:1, v/v for 1 hour at 0° C.).

Recombinant *P. vivax* Protein

VIVAX-1 is a recombinant protein containing approximately 60% of the entire CS protein from the Belem strain of *P. vivax*. It contains the repeat regions $(DRA\ A/D\ GQPAG)_{20}$ (Barr, P. J., H. L. Gibson, V. Enea, D. E. Arnot, M. R. Hollingdale and V. Nussenzweig; Expression in yeast of a *Plasmodium vivax* antigen of potential use in a human malaria vaccine; *J. Exp. Med.;* 165:1160–1171; 1987). $NS1_{81}V20$ (SKF/WRMAIR) vaccine is a fusion protein from *Eschertichia coli* that contains the 20 copies of the nonapeptide repeat present in the repeat region of the CS protein and 81 amino acids derived from the nonstructural protein gene of influenza A (Collins, W. E., R. S. Nussenzweig, W. R. Ballou, T. K. Ruebush II, E. H. Nardin, J. D. Chulay, W. R. Majarian, J. F. Young, G. F. Wasserman, I. Bathurst, H. L. Gibson, P. J. Barr, S. L. Hoffman, S. S. Wasserman, J. R. Broderson, J. C. Skinner, P. M. Procell, V. K. Filipski and C. L. Wilson; Immunization of *Saimiri sciureus boliviensis* with recombinant vaccines based on the circumsporozoite protein of *Plasmodium vivax; Am. J Trop. Med. Hyg.;* 40:455–464; 1989).

EXAMPLE 6
Immunofluorescent Antibody Technique

NVS3 activity was measured in the serum of the monkeys which received intravenous NVS3 prior to sporozoite challenge. Two-fold serial dilutions of sera were used in an IFAT with *P. vivax* sporozoites as the target antigen (Charoenvit, Y., M. F. Leef, L. F. Yuan, M. Sedegah and R. L. Beaudoin; Characterization of *Plasmodium yoelii* monoclonal antibodies directed against stage-specific sporozoite antigens; *Infect. Immunol.*; 55:604–608; 1987). To determine if NVS3 reacts with epitopes other than AGDR on sporozoites, aliquots of NVS3 at a concentration of 2.5 µg/ml were preincubated with varying amounts of the *P. vivax* peptide $(AGDR)_2$ or the unrelated peptide $(QGPGAP)_2$, a peptide from the repeat region of *P. yoelii* CS protein. The antibody-peptide mixtures were then incubated with *P. vivax* sporozoites and evaluated by IFAT to determine the ability of $(AGDR)_2$ to block the binding of NVS3 to sporozoites.

The immunofluorescent antibody studies show that NVS3 binds to *P. vivax* sporozoites but not to *P. yoelli* sporozoites. Furthermore, this binding is to a specific epitope; NVS3 binding to *P. vivax* sporozoites can be blocked by preincubation with the *P. vivax* octapeptide $(AGDR)_2$ but not with the *P. yoelii* dodecapeptide $(QGPGAP)_2$.

EXAMPLE 7
ELISA

NVS3 concentrations in sera from monkeys receiving NVS3 prior to sporozoite challenge was measured in ELISA using $(AGDR)_2$ as the target antigen. Serum dilutions (1:100) were incubated with $(AGDR)_2$-coated wells. The secondary antibody was horseradish peroxidase-labelled goat anti-mouse IgG. Optical density values for the serum samples were compared with standard values obtained by measuring the reactivity to $(AGDR)_2$ of known concentrations of NVS3 diluted in equivalent concentrations of Saimiri monkey serum.

Serum Levels of NVS3 and Anti-$(AGDR)_2$, Activity

Serum samples from the monkeys passively immunized with NVS3 were assayed for anti-sporozoite and anti-$(AGDR)_2$ activities. NVS3 passive transfer sera contains high levels of antibodies as determined by IFAT and ELISA (Table 2).

EXAMPLE 8
Inhibition of Antibody Activity in Sera From NS181V20-immunized Monkeys Serum from six monkeys immunized with $NS1_{81}V20$ were tested in ELISA for activity to $(AGDR)_2$ and VIVAX-1. Aliquots of each serum sample (1:250 final concentration) were incubated with varying concentrations of $(AGDR)_2$ or VIVAX-1 to determine if activity to the repeat region of the CS protein can be blocked. VIVAX-1 was used as the target antigen in an ELISA and *P. vivax* sporozoites were used as the target antigen in a parallel series of IFAT assays. In both cases, secondary antibody was goat anti-human IgG.

Antibody Activity in Sera From Monkeys Immunized with $NS1_{81}$ V20

Figure 3:
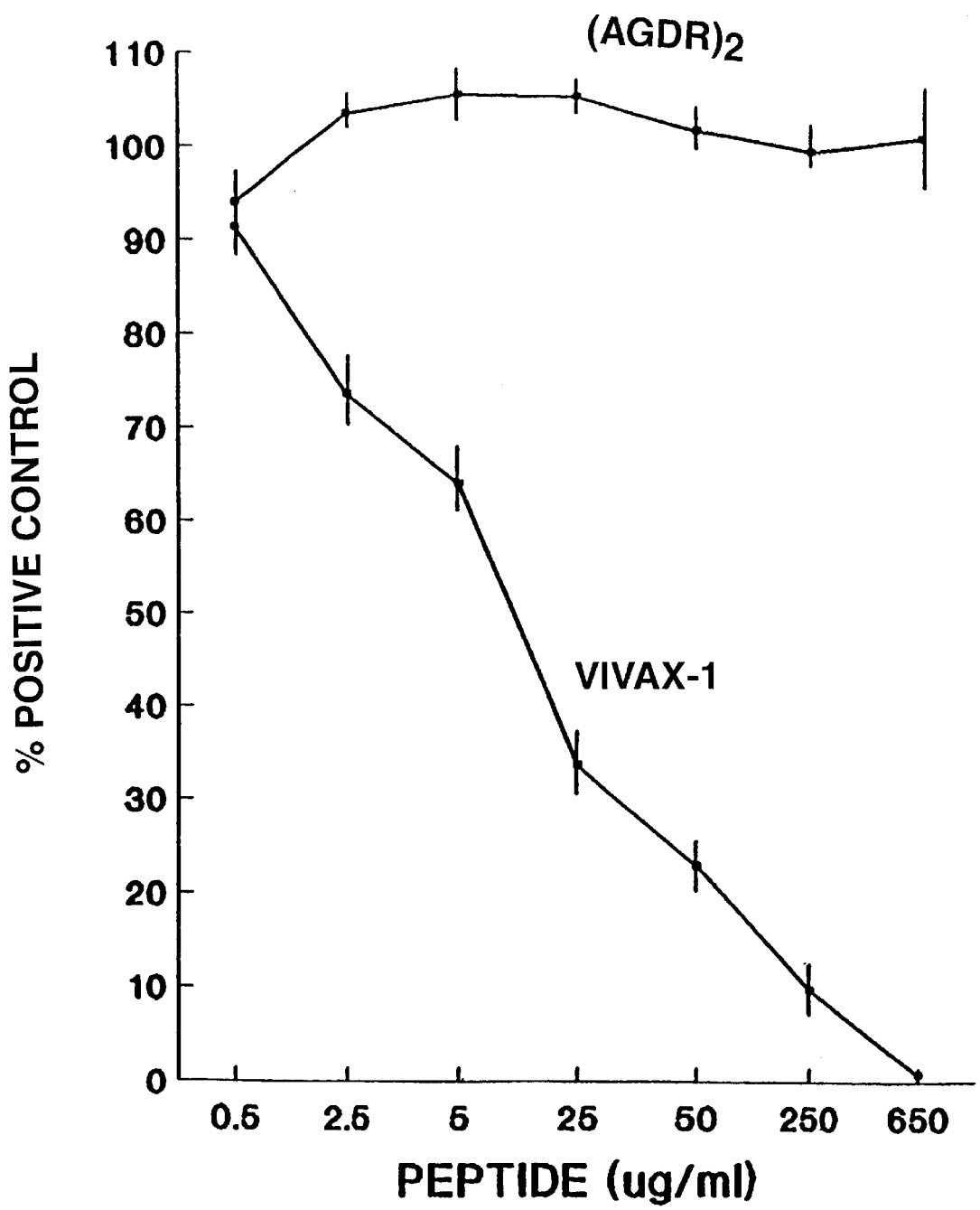
FIG. 3 is a graph of (AGDR)$_2$ and the recombinant vaccine VIVAX-1 incubated with aliquots of sera from monkeys immunized with NS1$_{81}$V2O. Final serum concentration was 1:250, final peptide concentrations are depicted along the X-axis. Vertical bars depict standard error.

Serum samples (1:100 and 1:500 final concentrations) from monkeys immunized with $NS1_{81}V20$ reacted will with VIVAX-1 but not with $(AGDR)_2$ in a direct ELISA. When these sera were preincubated with VIVAX-1, all anti-VIVAX-1 activity was removed; preincubation with $(AGDR)_2$ removed no activity (FIG. 3 wherein $(AGDR)_2$ and the recombinant vaccine VIVAX-1 were incubated with aliquots of sera from monkeys immunized with $NS1_{81}V2O$. Final serum concentration was 1:250, final peptide concentrations are depicted along the X-axis. Vertical bars depict standard error.). When similarly preincubated serum samples were tested in IFAT for anti-sporozoite activity, VIVAX-1 preincubation eliminated all anti-sporozoite activity in a VIVAX-1 concentration-dependent manner. Preincubation with $(AGDR)_2$ removed no activity (data not shown).

EXAMPLE 9
Inhibition of Liver Stage Development

The ability of NVS3 to inhibit the in vitro development of sporozoites in hepatocytes was measured following the technique of Millet and colleagues (Millet, P., W. E. Collins, L. Herman and A. H. Cochrane; *Plasmodium vivax:* In vitro development of exoerythrocytic stages in squirrel monkey hepatocytes and inhibition by an anti-*P. cynomolgi* monoclonal antibody; *Exp. Parasitol;* 69:91–93; 1989). Briefly, a monkey liver fragment was dissociated by collagenase perfusion and plated in 35 mm petri dishes. Equal volumes of serum (or NVS3) and sporozoite suspension were mixed and incubated at room temperature for 15 minutes. The NVS3-sporozoite mixtures were exposed to the hepatocytes for 2 hours then washed. Seven days post-exposure, the monolayers were fixed and schizonts counted microscopically.

Inhibition of Liver Stage Development

After incubation with either serum or NVS3, $2.5 \times 10^4$ *P. vivax* sporozoites were added to each monolayer of primary cultures of Saimiri hepatocytes. Results (Table 2) are expressed as the number of schizonts in two monolayers. Serum from NVS3-treated monkeys was very effective in reducing or eliminating schizont development.

The studies described here demonstrate for the first time that circulating antibodies to human malaria sporozoites can protect against sporozoite challenge. Four of six monkeys were completely protected; the remaining two had significantly prolonged prepatent periods when compared to control animals. Circulating antibodies to the *P. vivax* CS protein can protect against sporozoite-induced malaria. Although there has been a major emphasis on protection against malaria by active immunization with subunit vaccines, the above examples and data suggest that another strategy for protecting humans against malaria may be to use human monoclonal antibodies with specificities similar to NVS3 to provide passive protection during-short term exposure.

EXAMPLE 10

The monoclonal antibody NVS3 is used as a passive prophylactic agent by solubilization in an appropriate pharmaceutical injectable such as but not restricted to normal saline and subsequent injection into persons needing prophylactic protection from *P. vivax* malaria. The dose of the injected antibody will be adjusted to provide a protective level of circulating antibody. A dose between 50 to 1000 mg per individual may be preferred. The route of injection may be intravenous, intramuscular or subcutaneous.

EXAMPLE 11

The monoclonal antibody produced by the above cited hybridoma cell line is to be humanized by a method which will replace all of the mouse antbody molecule, except the antigen binding site with human antibody. This is genetically engineered by the method of Morrison et al. (PNAS USA, 81:6851, 1984), or other appropriate methods. mRNA from the NVS3-producing hybridoma is isolated and RNA-dependent DNA polymerase is used to produce an RNA/DNA hybrid. The RNA is then removed by treatment with RNAase. A Klenow fragment of DNA polymerase 1 is used to make double stranded DNA and treatment with EcoR 1 methylase blocks any EcoR 1 sites within the strand. EcoR 1 linkers are ligated to the ends of the cDNA which is then treated with EcoR 1. Selective ethanol precipitation is used to separate the cDNA from the linkers. The cDNA is then ligated into the EcoR 1 site of a lambda phage (e.g. g+11) and DNA is packaged in a commercial packaging extract. Once *E. coli* are exposed to the phages, they are plated and screened with cloned $V_H$ and $V_K$ or 1 genes as probes. The $V_H$ gene is spliced to human IgG C region gene using Sal 1 linkers. The $V_{K\,or\,1}$ gene is spliced to the human K or 1 light chain joining and C region exons. Both these chimeric gene constructs are then inserted into a vector. Both vectors must have the ability to grow in *E. coli*, possess a mammalian promoter and have different mammalian and bacterial drug resistance genes. The $V_H$ and $V_K$ or 1 containing constructs are transfected sequentially into an appropriate mouse myeloma cell line, such as J558L, by calcium phosphate precipitation. After one construct has been transfected into the host cell line, successful transfectants are selected for using the drug resistance gene in the vector. Successfully transfected cells then receive the second construct and are selected for by use of the second, and different, drug. The cells are then cloned by limiting dilution. Production of antibody having specificity for AGDR in ELISA will be used to screen the clones.

EXAMPLE 12

The humanized monoclonal antibody possissing the complimentarity determining region of NVS3 is used as a passive prophylactic agent by solubilization in an appropriate pharmaceutical injectable such as but not restricted to normal saline and subsequent injection into persons needing prophylactic protection from *P. vivax* malaria. The dose of the injected antibody will be adjusted to provide a protective level of circulating antibody. A dose between 50 to 1000 mg per individual may be preferred. The route of injection may be intravenous, intramuscular or subcutaneous.

TABLE 1

Prepatent periods and maximum parasitemia in monkeys passively immunized with the monoclonal antibody NVS3 and challenged with $10^4$ sporozoites of the Salvador I strain of *Plasmodium vivax.*

| Monkey No. | Antibody | Prepatent Period | Maximum Parasitemia per $mm^3$ | Maximum Parasitemia Day |
|---|---|---|---|---|
| SI-74 | NVS3/2 mg | 40 | 9,393 | 56 |
| SI-162 | NVS3/2 mg | NI | — | — |
| SI-218 | NV53/2 mg | 31 | 21,018 | 55 |
| SI-250 | NVS3/2 mg | NI | — | — |
| SI-251 | NVS3/2 mg | NI | — | — |
| SI-312 | NVS3/2 mg | NI | — | — |
| SI-323 | Try/2 mg | NI | — | — |
| SI-319 | Try/2 mg | 23 | 341 | 31 |
| SI-330 | Try/2 mg | 15 | 42,966 | 51 |
| SI-316 | Try/2 mg | 24 | 47,616 | 46 |
| SI-321 | Try/2 mg | 23 | 55,614 | 39 |
| SI-328 | Try/2 mg | 18 | 98,394 | 56 |
| SI-311* | None | 29 | 21 | 37 |
| SI-238* | None | 18 | 30,132 | 42 |
| SI-320 | None | 17 | 30,876 | 53 |
| SI-45* | None | 30 | 39,432 | 56 |
| SI-249 | None | 19 | 48,918 | 56 |
| SI-174 | None | 20 | 75,888 | 45 |

TABLE 1-continued

Prepatent periods and maximum parasitemia in monkeys passively immunized with the monoclonal antibody NVS3 and challenged with $10^4$ sporozoites of the Salvador I strain of *Plasmodium vivax.*

| Monkey No. | Antibody | Prepatent Period | Maximum Parasitemia per $mm^3$ | Maximum Parasitemia Day |
|---|---|---|---|---|
| SI-289 | None | z1 | 77,748 | 54 |
| SI-101* | None | 17 | 93,588 | 43 |
| SI-300 | None | 19 | 312,000 | 55 |

*Animals splenectomized on day 6; all others on day 7.

TABLE 2

NVS3 serum levels one hour after passive transfer as measured by immunofluorescent antibody technique with *Plasmodium vivax* sporozoites as antigen, ELISA with $(AGDR)_2$ as antigen and inhibition of sporozoite development in Saimiri monkey hepatocytes. Monkeys SI-74 through SI-312 received 2 mg of NVS3 while monkeys SI-316 through SI-321 received 2 mg of anti-trypanosoma monoclonal antibody. Serum samples taken from each animal immediately prior to NVS3 injection were all negative for anti-sporozoite activity in IFAT and below the sensitivity of the $(AGDR)_2$ ELISA.

| Monkey No. | IFAT Titer | ELISA $(AGDR)_2$ $\mu g/ml$ | Mean # Schizonts/ two 35 mm monolayers |
|---|---|---|---|
| SI-74 | 6400 | 14.3 ± 8.9 | 54/1.5* |
| SI-162(P) | 12,800 | 18.4 ± 14 | 44/0.5 |
| SI-218 | 3200 | 4.3 ± 2.6 | 51.5/1 |
| SI-250(P) | 6400 | 18.5 ± 5 | 49/0.5 |
| SI-251(P) | 6400 | 7.2 ± 3.6 | 37.5/1.5 |
| SI-312(P) | 6400 | 5.9 ± 3.5 | 36/0.0 |
| SI-316 | neg | neg | NT/31 |
| SI-319 | neg | neg | NT/10 |
| SI-321 | neg | neg | NT/22 |

NT = not tested
neg = below IFAT and ELISA sensitivity
IFAT titers = reciprocal of dilutions
(P) = protected in sporozoite challenge
*sera before NVS3 injection/sera 1 hour after NVS3 injection Obviously, many modifications and variations of the present invention are possible in light of the above teachings. It is therefore to be understood that, within the scope of the appended claims, the invention may be practiced otherwise than as specifically described.

REFERENCES

1. Institute of Medicine. Malaria: Obstacles and Opportunities. S. C. Oaks, V. S. Mitchell, G. W. Pearson and C. Carpenter, eds. National Academy Press, Washington D.C. (1991).
2. H. W. Mulligan, P. Russell and B. N. Mohan. *J.Mal.Inst.India* 4:25 (1941).
3. R. S. Nussenzweig, J. Vanderberg, H. Most and C. Orton. *Nature* 216:160 (1967).
4. D. F. Clyde, V. C. McCarthy, R. M. Miller and R. B. Hornick. *Am.J.Med.Sci.* 266: 398 (1973).
5. D. F. Clyde, V. C. McCarthy, R. M. Miller and W. E. Woodward. *Am.J.Trop.Med.Hyg.* 24:397 (1975).
6. D. F. Clyde, H. Most, V. C. McCarthy and J. P. Vanderberg. *Am.J.Med.Sci.* 266: 169 (1973).
7. K. H. Rieckmann et al. *Trans.R.Soc.Trop.Med.Hyg.* 68: 258 (1974).
8. K. H. Rieckmann, R. L Beaudoin, J. S. Cassells and D. W. Sell. *Bull. W.H.O.* 57: 261 (1979).
9. D. Herrington et al. *Am.J. Trop.Med.Hyg.* 45: 539 (1991).

10. J. E. Egan et al. *Am.J.Trop.Med.Hyg.* (1992) (In Press).
11. R. Edelman et al. *J.Infect.Dis.* 168: 1066 (1993).

What we claim is:

1. A formulation protective against *Plasmodium vivax* for a time commensurate with the time monoclonal antibody Navy Vivax Sporozoite 3 (HB10615) remains at pharmacologically active levels in a subject's blood stream, comprising a pharmaceutical amount sufficient to provide passive immunization of Navy Vivax Sporozoite 3 (HB10615) in a pharmaceutically suitable injectable solution.

2. The formulation of claim 1 containing between about 2 and 30 mg of Navy Vivax Sporozoite 3 (HB10615).

3. The formulation of claim 1 containing about 2 mg of Navy Vivax Sporozoite 3 (HB10615).

4. A method of providing protection from *Plasmodium vivax* induced malaria for subjects experiencing exposure to infected mosquitoes, for a time commensurate with the time monoclonal antibody Navy Vivax Sporozoite 3 (HB10615) remains at pharmacologically active levels in the subject's blood stream, that comprises introducing and circulating the antibody Navy Vivax Sporozoite 3 (HB10615) in the subject's blood stream.

5. The method of claim 4 wherein between about 2 to 30 mg of Navy Vivax Sporozoite 3 (HB10615) is introduced into a subject's blood stream.

6. The method of claim 4 wherein about 2 mg of Navy Vivax Sporozoite 3 (HB10615) is introduced into a subject's blood stream.

7. The method of claim 4 wherein AGDR sites on the CS protein of *Plasmodium vivax* are bound by the Navy Vivax Sporozoite 3 (HB10615).

8. A humanized antibody capable of providing passive protection against *Plasmodium vivax* wherein said antibody has a variable region comprising the hyper variable regions of the heavy and light chains of monoclonal antibody Navy Sporozoite 3 (HB10615) and human antibody framework regions.

9. A mouse/human chimeric antibody comprising the heavy and light chain variable regions of monoclonal antibody Navy Sporozoite 3 (HB10615) and a human constant region.

* * * * *